United States Patent [19]
Lee et al.

[11] Patent Number: 6,129,863
[45] Date of Patent: Oct. 10, 2000

[54] CLEAN GENERATION OF A PERFLUOROARYL GRIGNARD REAGENT

[75] Inventors: John Y. Lee; David W. Owens; Charles R. Everly; Ronny W. Lin, all of Baton Rouge, La.; John M. Power, Kingwood, Tex.; Steven P. Diefenbach, Baton Rouge, La.; Niomi L. Krzystowczyk, Orangeburg, S.C.

[73] Assignee: Albemarle Corporation, Richmond, Va.

[21] Appl. No.: 09/216,463

[22] Filed: Dec. 18, 1998

[51] Int. Cl.[7] .................................. C07F 3/02; C07F 5/02
[52] U.S. Cl. ............................. 260/665 G; 568/1
[58] Field of Search ............................. 260/665 G; 268/1

[56] References Cited

U.S. PATENT DOCUMENTS

| | | | |
|---|---|---|---|
| 5,362,423 | 11/1994 | Ikeda et al. | 260/665 R |
| 5,399,780 | 3/1995 | Ikeda et al. | 568/1 |
| 5,473,036 | 12/1995 | Piotrowski et al. | 528/4 |
| 5,600,004 | 2/1997 | Diefenbach | 268/1 |
| 5,693,261 | 12/1997 | Krzystowczyk et al. | 260/665 G |

FOREIGN PATENT DOCUMENTS

| | | |
|---|---|---|
| 0604963 | 7/1994 | European Pat. Off. . |
| 0728760 | 8/1996 | European Pat. Off. . |

OTHER PUBLICATIONS

Nield, E. et al., "Aromatic Polyfluro–compounds. Part I. The Synthesis of Aromatic Polyfluoro–compounds from Pentalflurobenzene", J. Chem. Soc., 1959, pp. 166–171.

Respess, W. L. et al., "A New Synthesis of Perfluoroaromatic Grignard Reagents", J. Organometal. Chem., vol. 18, 1969, pp. 263–274.

Respess, William L. et al., "Synthesis of Some Pentafluorophenylmagnesium Compounds", J. Organometal. Chem., vol. 11, 1968, pp. 619–622.

Harper, Robert J. et al., "Reactions of Organometallics with Fluroaromatic Compounds[1]", J. Organic Chem., vol. 29, 1964 pp. 2385–2389.

Respess, W. L. et al., "The Preparation of a Grignard Reagent From Hexaflurobenzene by the Entrainment Technique", J. Organometal. Chem., vol. 19, 1969, pp. 191–195.

Jukes, A. E. et al., "(Pentafluorophenyl)Magnesium Chloride", J. Organometal. Chem., vol. 17, 1969, pp. 145–148.

Kobayashi, Hiroshi et al., "Synthesis of Trifluoromethylated Tetraphenylborates and Solvent–extraction Properties of their Ion–associates with Alkali–metal Ions", Rep. Asahi Glass Found. Ind. Technol, vol. 42, 1983, pp. 137–145.

Zakharkin, L. I. et al., "Effect of Solvents on Reactions of Organometallic Compounds; II. Exchange of Radicals Between $Rm_gX$ And R'X", J. Organometal. Chem., vol. 2, 1964, pp. 309–313.

*Primary Examiner*—Paul F. Shaver
*Attorney, Agent, or Firm*—Philip M. Pippenger

[57] ABSTRACT

Perfluoroaryl Grignard reagents are produced from a hydrocarbyl Grignard reagent and polyhaloaromatic compounds via separate additions of different polyhaloaromatic compounds, such that the conversion of hydrocarbyl Grignard reagent to the desired perfluoroaryl Grignard reagent is essentially complete, and thus the reaction product is free or essentially free of agents that may negatively affect subsequent reactions. The perfluoroaryl Grignard reagents may be further reacted with boron trihalides in order to obtain tris(perfluoroaryl)boranes or tetrakis(perfluoroaryl)borates.

52 Claims, No Drawings

CLEAN GENERATION OF A PERFLUOROARYL GRIGNARD REAGENT

TECHNICAL FIELD

This invention concerns a process in which polyhaloaromatic compounds are converted to perfluoroaryl Grignard reagents via reaction with hydrocarbyl Grignard reagents, and further processes that utilize these perfluoroaryl Grignard reagents.

BACKGROUND

Perfluoroaryl Grignard reagents are useful in the synthesis of metal and metalloid perfluoroaryl compounds. Many preparations of perfluoroaryl Grignard reagents are known in the literature, some of which call for stoichiometric amounts of Grignard reagent and the polyhaloaromatic compound, *J. Organomet. Chem.*, 1969, 18, 263–274, and *J. Organomet. Chem.*, 1968, 11, 619–622. Others describe the use of excess Grignard reagent, *J. Org. Chem.*, 1964, 29, 2385–2389, and *J. Organomet. Chem.*, 1969, 19, 191–195. While it will not be considered further here, it should be noted that perfluoroaryl Grignard reagents have been generated in which the perfluoroaryl Grignard reagent is made directly from Mg metal and the polyhaloaromatic compound, as reported in *J. Chem. Soc.*, 1959, 166–171, and *J. Org. Chem.*, 1964, 29, 2385–2389. Two U.S. patents describe methods for obtaining perfluoroaryl Grignard reagents, one with the Grignard reagent in excess, U.S. Pat. No. 5,362,423, and the other with the polyhaloaromatic compound in excess, U.S. Pat. No. 5,600,004.

Separation of unreacted alkyl Grignard reagent and polyhaloaromatic compound starting materials from the reaction mixture is often desired, due to their interference in subsequent syntheses, but such separation is not always feasible.

THE INVENTION

This invention makes possible the formation of a perfluoroaryl Grignard reagent from a hydrocarbyl Grignard reagent and polyhaloaromatic compounds via separate additions of different polyhaloaromatic compounds, such that the conversion of hydrocarbyl Grignard reagent to the desired perfluoroaryl Grignard reagent is essentially complete, and thus the reaction product is free or essentially free of agents that may negatively affect subsequent reactions.

A first embodiment of this invention entails in step a) forming a mixture comprising (i) hydrocarbyl Grignard reagent, (ii) at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, and (iii) an anhydrous liquid organic reaction medium. The molar ratio of (i) to (ii) is greater than one, such that a reaction product mixture is formed comprising perfluoroaryl Grignard reagent and excess hydrocarbyl Grignard reagent. In step b) at least a portion of the reaction product mixture produced in a) is mixed with an amount of at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, at least sufficient to react with the excess hydrocarbyl Grignard reagent, which thereby produces a further reaction product mixture composed predominately of perfluoroaryl Grignard reagent and anhydrous liquid organic reaction medium.

Another embodiment of the invention involves a process which comprises a) reacting, in a liquid organic reaction medium, at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, with a stoichiometric excess of a hydrocarbyl Grignard reagent to produce a reaction product mixture comprising perfluoroaryl Grignard reagent and unreacted hydrocarbyl Grignard reagent. In step b), at least a portion of the reaction product mixture produced in a) is contacted with a polyhaloaromatic compound to convert at least a portion of said unreacted hydrocarbyl Grignard reagent into perfluoroaryl Grignard reagent.

Still another embodiment of this invention entails a process which comprises a step b) in which a mixture comprising a perfluoroaryl Grignard reagent, a hydrocarbyl Grignard reagent, and a liquid organic medium is contacted with at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, in an amount at least equivalent to the amount of said hydrocarbyl Grignard reagent. The resultant mixture is maintained at a temperature at least high enough to cause hydrocarbyl Grignard reagent to be converted into perfluoroaryl Grignard reagent.

In another embodiment of this invention, a) a mixture is formed comprising (i) hydrocarbyl Grignard reagent, (ii) at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, and (iii) an anhydrous liquid organic reaction medium. In this mixture, the molar ratio of (i) to (ii) is greater than one, such that a reaction product mixture is formed comprising perfluoroaryl Grignard reagent and excess hydrocarbyl Grignard reagent. In step b), at least a portion of the reaction product mixture produced in a) is mixed with an amount of at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, such amount being in excess relative to the excess hydrocarbyl Grignard reagent such that a further reaction product mixture is produced composed predominately of perfluoroaryl Grignard reagent, anhydrous liquid organic reaction medium, and unreacted polyhaloaromatic compound. In step c), a boron trihalide or a boron trihalide-solvent complex is mixed with at least a portion of the reaction product mixture produced in b) in proportions such that a tris(perfluoroaryl)borane is produced.

A further embodiment of this invention involves a) forming a mixture comprising (i) hydrocarbyl Grignard reagent, (ii) at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, and (iii) an anhydrous liquid organic reaction medium. The molar ratio of (i) to (ii) added to the mixture is greater than one, such that a reaction product mixture is formed comprising perfluoroaryl Grignard reagent and excess hydrocarbyl Grignard reagent. In step b), at least a portion of the reaction product mixture produced in a) is mixed with an amount of at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, such amount being in excess relative to the hydrocarbyl Grignard reagent such that there is produced a further reaction product mixture composed predominately of perfluoroaryl Grignard reagent, anhydrous liquid organic reaction medium, and unreacted polyhaloaromatic compound. In step c), a boron trihalide or a boron trihalide-solvent complex is mixed with at least a portion of the reaction product mixture produced in step b) in proportions such that a salt of a tetrakis(perfluoroaryl)borate anion is produced.

Further embodiments of the invention will be apparent from the ensuing description and appended claims.

The hydrocarbyl Grignard reagent is made by combining a hydrocarbyl halide and Mg in a suitable reaction medium, either the medium used for the process, or a separate medium, which is then added to the liquid organic reaction medium of the process. Alternatively, commercially available hydrocarbyl Grignard reagents may be used. The word hydrocarbyl is defined as any monovalent group derived from a linear, branched, or cyclic $C_1$ to $C_{20}$ hydrocarbon. Examples of hydrocarbyl Grignard reagents include ethylmagnesium chloride, sec-butylmagnesium bromide, cyclopentenylmagnesium chloride, cyclohexylmagnesium bromide, 3-hexenylmagnesium iodide, 4-methylcyclooctylmagnesium iodide, 6-ethyldodecylmagnesium bromide, and eicosylmagnesium chloride. Short-chain alkyl Grignard reagents, e.g., $C_1$ to $C_6$, are preferred hydrocarbyl Grignard reagents, and the preferred halogen atom of the hydrocarbyl Grignard reagent is a bromine atom. Isopropylmagnesium bromide is the most highly preferred hydrocarbyl Grignard reagent.

Throughout this document, the term "polyhaloaromatic compound" shall be understood to mean, as described above, an aromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group. The aromatic ring of the polyhaloaromatic compound may be, but is not limited to, benzene, naphthalene, anthracene, biphenyl, phenanthrene, or indene. Benzene is the preferred aromatic moiety. The hydrocarbyl groups of the polyhaloaromatic compounds are preferably aryl groups or $C_1$ to $C_{10}$ alkyl groups. Examples of suitable hydrocarbyl groups are methyl, ethyl, isopropyl, tert-butyl, cyclopentyl, methylcyclohexyl, decyl, phenyl, tolyl, xylyl, and naphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The perfluorinated hydrocarbyl groups include alkyl and aryl perfluorocarbons; suitable perfluorinated hydrocarbyl groups are, for example, trifluoromethyl, pentafluoroethyl, pentafluorophenyl, and heptafluoronaphthyl. Examples of polyhaloaromatic compounds that can be used in the practice of this invention include 1-bromo-4-(trifluoromethyl)-tetrafluorobenzene, 4-chloro-4'-(methoxy)-octafluorobiphenyl, 1-bromo-2-(isopropoxy)-hexafluoronaphthalene, 7-bromo-9,10-bis(heptafluoropropyl)-heptafluoroanthracene, 1-chloro-9,10-bis(p-tolyl)-heptafluorophenanthrene, and 1-bromo -1-(trifluoromethyl)-tetrafluoroindene. It is preferred that at most two substituents on the ring of the polyhaloaromatic compound are hydrocarbyl, perfluorinated hydrocarbyl, or alkoxy, while the rest of the substituents, except the one atom which is hydrogen or a halogen atom other than fluorine, are fluorine atoms.

It is highly preferred to use polyhaloaromatic compounds in which the all of the substituents, except the one atom which is hydrogen or a halogen atom other than fluorine, are fluorine atoms. Examples of such compounds are pentafluorobenzene, chloropentafluoro-benzene, bromopentafluorobenzene, iodopentafluorobenzene, 4-chlorononafluorobiphenyl, 2-bromononafluorobiphenyl, 2,2',3,3',4,5,5',6,6'-nonafluorobiphenyl, 1-chloroheptafluoronaphthalene, 2-bromoheptafluoronaphthalene, 7-chlorononafluoroanthracene, 9-bromononafluorophenanthrene, and analogous compounds.

The polyhaloaromatic compound or compounds added in both steps a) and b) of the process contain a site reactive toward a hydrocarbyl Grignard reagent; this site of the polyhaloaromatic compound is an iodine, bromine, chlorine, or hydrogen atom. Preferably, the polyhaloaromatic compound added in a) has a chlorine atom as its Grignard-reactive site, while the polyhaloaromatic compound added in b) has either a bromine atom or a hydrogen atom as its Grignard-reactive site. The most highly preferred polyhaloaromatic compound in step a) is chloropentafluorobenzene; in step b), it is bromopentafluorobenzene.

In both steps a) and b), a single polyhaloaromatic compound may be added, or a mixture of two or more such compounds may be used. When a mixture of different perfluoroaryl Grignard reagents is desired, a mixture of polyhaloaromatic compounds with different aromatic rings is added. For example, a mixture of chloropentafluorobenzene and 2-chlorononafluoro-biphenyl may be added in step a), followed by the addition of bromopentafluorobenzene and 2,2',3,3',4,4',5,5',6-nonafluorobiphenyl. The addition of two compounds, alike save the Grignard-reactive substituent, will yield one perfluoroaryl Grignard reagent. This is the preferred embodiment of the invention, and it is preferred that the mixture of polyhaloaromatic compounds is added in step b) rather than in step a). It is highly preferred to add chloropentafluorobenzene in step a) and either bromopentafluorobenzene alone or a mixture of bromopentafluorobenzene and pentafluorobenzene in step b); most highly preferred in step b) is the addition of only bromopentafluorobenzene.

Preferably, the liquid organic reaction medium is an ether-containing medium. This medium may be comprised of one or more ethers, and may, at various points, also contain one or more other types of components, such as hydrocarbons or hydrocarbyl halides. Any of a variety of monoethers or polyethers may be used, including diisopropyl ether, dibutyl ether, tetrahydofuran, 1,4-dioxane, cyclohexylmethyl ether, diglyme, triglyme, and tetraglyme. Diethyl ether is a preferred liquid organic reaction medium in the practice of this invention.

The amount of hydrocarbyl Grignard reagent added in step a) of the process should be in molar excess of the amount of polyhaloaromatic compound added in step a) of the process. The preferred molar excess is in the range of from about 1.01 mole hydrocarbyl Grignard reagent per mole polyhaloaromatic compound to about 1.25 mole hydrocarbyl Grignard reagent per mole polyhaloaromatic compound. Most desirable is a molar excess of about 1.05 to about 1.15 mole hydrocarbyl Grignard reagent per mole polyhaloaromatic compound.

In step b) of the process of this invention, the amount of polyhaloaromatic compound(s) is in at least sufficient excess relative to the excess hydrocarbyl Grignard reagent present such that the reaction product mixture comprises excess, unreacted polyhaloaromatic compound. Sufficient excess of polyhaloaromatic compound in b) is a molar amount larger than the excess molar amount of hydrocarbyl Grignard reagent added in a). It is necessary to add more than the stoichiometric amount of polyhaloaromatic compound to react with the expected excess hydrocarbyl Grignard reagent in order to drive the reaction, much as the excess hydrocarbyl Grignard reagent drives the reaction in a). The molar amount of polyhaloaromatic compound typically ranges from about 1.01 to about 4 moles per excess mole of hydrocarbyl Grignard reagent, with the preferred ranges being from about 1.5 to about 2.5 moles per excess mole of hydrocarbyl Grignard reagent. The unreacted polyhaloaromatic compound(s) in the reaction product mixture produced in step b) may be reacted with more hydrocarbyl Grignard reagent via back-titration in order to form more perfluoroaryl Grignard reagent.

Steps a) and b) can be conducted at any temperatures below the thermal decomposition temperature of the reactants and desired products of the reactions, provided that (i) the reaction mixtures are in the liquid state under the temperature and pressure conditions being used, and (ii) the desired reaction takes place at a suitable rate of reaction under the temperature and pressure conditions being used. Reaction temperatures in steps a) and b) are often within the range of from about 0° C. to about 60° C., and more more often the temperature is in the range of from about 25° C. to about 58° C. When the reactions are conducted at atmospheric pressure or at elevated pressures of up to about 20 psig (about 240 kPa), it is preferred to operate at temperatures in the range of from about 45° C. to about 56° C. Depending on the reactants and solvents being used, it may be necessary to operate under elevated pressures when using temperatures above about 60° C. In either step a) or b), or both, the mixture can be heated to a specific temperature throughout the entire reaction period, or the temperature may be increased or decreased one or more times during the reaction period, provided of course that the temperature does not exceed the thermal decomposition temperature of the desired product of the reaction. In both steps a) and b) of the process, it is preferred to heat the mixture after the various components have been added, although one or more preheated feeds may be employed.

While the contact time for the various components of the reaction can be anywhere from two to twenty hours, a preferred range is from about three to about fifteen hours. The contact time is more preferably from about four to about ten hours.

In a highly preferred practice of the invention, perfluoroaryl Grignard reagents are produced when the hydrocarbyl Grignard reagent is isopropylmagnesium bromide; the polyhaloaromatic compound in step a) is chloropentafluorobenzene; the polyhaloaromatic compound in step b) is bromopentafluorobenzene; and (iii) in a) is a liquid ethereal reaction medium. The reaction product mixture produced in b) is thus composed predominately of pentafluorophenylmagnesium bromide, isopropyl chloride, isopropyl bromide, bromopentafluorobenzene, and liquid ethereal reaction medium. The bromopentafluorobenzene in the reaction product mixture produced in b) is then consumed in situ by back-titration with isopropylmagnesium bromide to form more pentafluorophenylmagnesium bromide.

The term "boron trihalide" includes boron trifluoride, boron trichloride, boron tribromide, boron triiodide, or any mixed-halogen boron trihalide, and the solvent-complexed forms of these compounds. The preferred boron trihalide for this embodiment is boron trifluoride and its solvent complexes, such as, for example, boron trifluoride diethyl etherate complex.

It is preferred that the boron trihalide is dissolved in a solvent. Preferred solvents are ethers; the highly preferred solvent is diethyl ether. Because the boron trihalide solution will be mixed with the perfluoroaryl Grignard reagent, the solvent is necessarily anhydrous, although traces of moisture can be tolerated. If the solvent is too wet or the reactor contains moisture, the amount of perfluoroaryl Grignard reagent needs to be increased to maintain the the ratio of perfluoroaryl Grignard reagent to boron trihalide.

At least a portion of the unreacted polyhaloaromatic compound may be recovered and recycled to step(s) a) and/or b) after either the tris(perfluoroaryl)borane or the tetrakis(perfluoroaryl)borate anion is produced. In some embodiments, other polyhaloaromatic compounds than the unreacted polyhaloaromatic compound from step b) are present, and are also recovered after production of the tris(perfluoroaryl)borane or the tetrakis(perfluoroaryl)borate anion. Methods for removal and recovery of components include distillation, stripping at reduced pressure, or the like.

To produce tris(perfluoroaryl)boranes, the ratio of perfluoroaryl Grignard reagent to boron trihalide or boron trihalide solvent complex normally is in the range of from at least about 2.7:1 to about 3.3:1. Ratios greater than about 3.3:1 yield larger amounts of the corresponding tetrasubstituted borate anion, while ratios less than about 2.7:1 yield larger amounts of disubstituted borane, both of which are undesired side products in this embodiment of the invention. Preferred ratios are in the range of from about 2.9:1 to about 3.15:1, where anion formation is minimized. Most preferred are ratios in a range from about 3.0:1 to about 3.09:1.

During initial mixing of the boron trihalide solution and the reaction product mixture produced in b), when proportions of perfluoroaryl Grignard reagent and boron trihalide are such that a tris(perfluoroaryl)borane will be produced, the temperature may range from about −20° C. to about 5° C. It is more preferred to keep the initial mixing temperature between about −15° C. and about 3° C. Highly preferable is a range from about −10° C. to about 0° C. The time for initial mixing may range from about 5 minutes to two hours. More preferable is a mixing time ranging from about 10 minutes to about one hour; most preferred is a time between about 15 minutes and about 45 minutes. The temperature in step c) after initial mixing may range from about −15° C. to about 40° C.; a more preferable range is from about −10° C. to about 35° C. A range from about 0° C. to about 25° C. is most preferred. While the contact time for the various components in step c) can be anywhere from three to forty hours, a more useful range is from about five to about thirty hours. The contact time is preferably from about ten to about twenty hours.

In order to produce tetrakis(perfluoroaryl)borate anions, the ratio of perfluoroaryl Grignard reagent to boron trihalide or boron trihalide-solvent complex generally is in the range of from at least about 3.8:1 to about 7.0:1. Ratios less than about 3.8:1 yield larger amounts of the corresponding trisubstituted borane, an undesired side product in this embodiment. Preferred ratios are in the range from about 4.0:1 to about 5.0:1, where borane formation is minimized. Most preferred are ratios from about 4.2:1 to about 4.5:1.

The temperature during initial mixing of the boron trihalide solution and the reaction product mixture produced in b), when proportions of perfluoroaryl Grignard reagent and boron trihalide are such that a tetrakis(perfluoroaryl)borate anion will be produced, may range from about 0° C. to about 50° C.; highly preferable is a range from about 15° C. to about 35° C. The time for initial mixing may range from about 5 minutes to two hours. More preferable is a mixing time ranging from about 10 minutes to about one hour; most preferred is a time between about 15 minutes and about thirty minutes. The temperature after initial mixing in step c) typically ranges from about 20° C. to about 60° C.; a more preferable range is from about 35° C. to about 60° C. A range from about 48° C. to about 58° C. is most preferred, especially when operating at pressures in the range of about 0 to about 20 psig (about 100 to about 240 kPa). While the contact time for the various components in step c) can be anywhere from one to twenty-four hours, a more useful range is from about three to about twenty hours. The contact time is preferably from about five to about ten hours.

For a highly preferred practice of this invention when producing tris(perfluoroaryl)boranes, the hydrocarbyl Grignard reagent is isopropylmagnesium bromide; the polyhaloaromatic compound in step a) is chloropentafluorobenzene; the polyhaloaromatic compound in step b) is bromopentafluorobenzene; and (iii) is a liquid ethereal reaction medium. The reaction product mixture produced in b) is composed predominately of pentafluorophenylmagnesium bromide, isopropyl chloride, isopropyl bromide, bromopentafluorobenzene, and liquid ethereal reaction medium. The bromopentafluorobenzene present in the reaction product mixture produced in b) is consumed in situ by back-titration with isopropylmagnesium bromide prior to step c), forming more pentafluorophenylmagnesium bromide. The boron trihalide is boron trifluoride or a boron trifluoride etherate, and the proportions in step c) are such that the molar ratio of pentafluorophenyl Grignard reagent to boron trifluoride is in the range of about 2.7:1 to about 3.30:1.

A highly preferred practice of the invention when it is desired to produce tetra-kis(perfluoroaryl)borate anions are is as follows: the hydrocarbyl Grignard reagent is isopropylmagnesium bromide; the polyhaloaromatic compound in step a) is chloropentafluorobenzene; the polyhaloaromatic compound in b) is bromopentafluorobenzene; and (iii) is a liquid ethereal reaction medium. The reaction product mixture produced in b) is composed predominately of pentafluorophenylmagnesium bromide, isopropyl chloride, isopropyl bromide, bromopentafluorobenzene, and liquid ethereal reaction medium. The bromopentafluorobenzene present in the reaction product mixture produced in b) is consumed in situ by back-titration with isopropylmagnesium bromide prior to step c) in order to form more pentafluorophenylmagnesium bromide. In step c), the boron trihalide is boron trifluoride or a boron trifluoride-solvent complex, and the proportions are such that the molar ratio of pentafluorophenyl Grignard reagent to boron trifluoride is in the range of about 3.8:1 to about 7:1.

The following examples are presented for purposes of illustration, and are not intended to impose limitations on the scope of this invention.

EXAMPLE 1

To a diethyl ether solution of isopropyl magnesium bromide, chloropentafluorobenzene is added at 0° C. to 40° C. under nitrogen with stirring in a period of thirty minutes, such that the isopropyl magnesium bromide is in 1.03 to 1.05 molar excess of the chloropentafluorobenzene. The mixture is stirred at 47° C. to 53° C.; after 5 to 10 hours, bromopentafluorobenzene is added to react with the excess isopropyl magnesium bromide, and the mixture is stirred at 25° C. for 1 hour. Any excess bromopentafluorobenzene is back-titrated in situ with isopropyl magnesium bromide to form more $C_6F_5MgBr$. The yield of $C_6F_5MgBr$ is 96.1%, and 3.9% $C_6F_5Cl$ remained, as determined by $^{19}F$ NMR, using $C_6H_5CF_3$ as a reference; no trace of iPrMgBr was seen with $^1H$ NMR.

EXAMPLE 2

Isopropyl magnesium bromide (30.0 g, 64.4mmol.) and 22.0 g dry diethyl ether are charged to a reaction vessel. Chloropentafluorobenzene (10.87 g, 53.7mmol.) is added at 38° C. to 39.7° C. under nitrogen with stirring in a period of one hour. The temperature of the mixture is raised to 47° C. during one hour with concurrent evaporation of about 20 g of diethyl ether, and the mixture is stirred at 44° C. to 47° C. for 11 hours. The mixture is then cooled to 20° C. The yield of $C_6F_5MgBr$ is 97.3%, with 2.5 to 2.7% $C_6F_5Cl$ and 8% iPrMgBr remaining, as determined by NMR, using $C_6H_5CF_3$ as a reference. To convert the 8% iPrMgBr to $C_6F_5MgBr$ and iPrBr, bromopentafluorobenzene is added, and the reaction mixture is stirred at 20° C. for thirty minutes.

EXAMPLE 3

Isopropyl magnesium bromide (10.0 g, 22.8mmol.) and 8.0 g dry diethyl ether are charged to a reaction vessel under nitrogen; the solution is cooled to 5° C. to 10° C. A mixture of chloropentafluorobenzene (2.03 g, 10mmol.) and pentafluorobenzene (1.68 g, 10mmol.) is added to the vessel at 10° C. to 38° C. under nitrogen with stirring during a three hour period. The reaction mixture is stirred at 46° C. and 14 psig (about 198 kPa) for three hours, followed by stirring at 55° C. to 60° C. and 20 psig (about 240 kPa) for eight hours. The mixture is cooled to 22° C., and NMR spectra are recorded, showing 99.7% conversion of chloropentafluorobenzene and 68% conversion of pentafluorobenzene. The reaction mixture is then stirred at 55° C. to 57° C. After 11 hours, 100% conversion of chloropentafluorobenzene and 81% conversion of pentafluorobenzene is seen by NMR. An additional 3.0 millimoles of pentafluorobenzene are added to the reaction mixture, which is then heated at 60° C. to 63° C. and 18 to 20 psig (about 225 to about 240 kPa) for 12 hours. NMR data now show 100% conversion of chloropentafluorobenzene, 100% conversion of isopropylmagnesium bromide, and 3.34 mlllimoles of unreacted pentafluorobenzene. The yield of $C_6F_5MgBr$ is 88%, based on total chloropentafluorobenzene and pentafluorobenzene, as determined by NMR, with $C_6H_5CF_3$ as a reference.

EXAMPLE 4

Neat $BF_3 \cdot OEt_2$ is added to a solution of $C_6F_5MgBr$ in diethyl ether at 22° C. to 35° C. under nitrogen with stirring in a fifteen minute period, such that the molar ratio of $C_6F_5MgBr$ to $BF_3$ is 4.3:1. The mixture is stirred at 50° C. to 57° C. under pressure for 10 hours. The yield of $BrMgB(C_6F_5)_4$ is 93%, as determined by $^{19}F$ NMR, using $C_6H_5CF_3$ as a reference, based on the amount of $BF_3 \cdot OEt_2$ added.

EXAMPLE 5

Neat $BF_3 \cdot OEt_2$ is added to a solution of $C_6F_5MgBr$ in diethyl ether at −10° C. to −2° C. under nitrogen with stirring in a thirty minute period, such that the molar ratio of $C_6F_5MgBr$ to $BF_3$ is 3.09:1. The mixture is stirred at −9° C. to 24° C. for 16 to 18 hours. The yield of $B(C_6F_5)_3 OEt_2$ is 85.3%, and there are 1.88% $BrMgB(C_6F_5)_4$, 1.62% $C_6F_5H$, plus unknowns, present as impurities, as determined by $^{19}F$ NMR, using $C_6H_5CF_3$ as a reference, based on the amount of $BF_3 \cdot OEt_2$ added.

EXAMPLE 6

$C_6F_5MgBr$ in diethyl ether is cooled under nitrogen to 1° C. Neat $BF_3 \cdot OEt_2$ is added dropwise to the $C_6F_5MgBr$ solution at 1° C. to 4° C. under nitrogen with stirring in a forty minute period, such that the molar ratio of $C_6F_5MgBr$ to $BF_3 \cdot OEt_2$ is 3.065:1. The mixture is stirred and heated to 10° C. for 1 hour, to 18° C. for another hour, and then at 18° C. to 21° C. for nine hours. The yield of $B(C_6F_5)_3 \cdot OEt_2$ is 84.8%, based on $BF_3$ $OEt_2$; the yield is 82.9%, based on $C_6F_5MgBr$, both as determined by NMR with $C_6H_5CH_3$ as reference.

EXAMPLE 7

The procedure of Example 6 was followed, except that the molar ratio of $C_6F_5MgBr$ to $BF_3 \cdot OEt_2$ is 3.05:1. The yield of $B(C_6F_5)_3 OEt_2$ is 82%, based on $C_6F_5MgBr$.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
    a) forming a mixture comprising (i) hydrocarbyl Grignard reagent, (ii) at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, and (iii) an anhydrous liquid organic reaction medium, in which the molar ratio of (i) to (ii) is greater than 1, such that a reaction product mixture is formed comprising perfluoroaryl Grignard reagent and excess hydrocarbyl Grignard reagent; and
    b) mixing with at least a portion of said reaction product mixture produced in a) an amount of at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, at least sufficient to react with said excess hydrocarbyl Grignard reagent to thereby produce a further reaction product mixture composed predominately of perfluoroaryl Grignard reagent and anhydrous liquid organic reaction medium.

2. A process as in claim 1 wherein the hydrocarbyl Grignard reagent is isopropylmagnesium bromide.

3. A process as in claim 1 wherein in a) the substituent other than fluorine in said at least one polyhaloaromatic compound is a chlorine atom.

4. A process as in claim 1 wherein in b) the substituent other than fluorine in said at least one polyhaloaromatic compound is a bromine atom.

5. A process as in claim 1 wherein in b) the substituent other than fluorine in said at least one polyhaloaromatic compound is a hydrogen atom.

6. A process as in claim 1 wherein in a) all of the substituents selected from fluorine atoms, hydrocarbyl groups, alkoxy groups, or perfluorinated hydrocarbyl groups are fluorine atoms.

7. A process as in claim 1 wherein in b) all of the substituents selected from fluorine atoms, hydrocarbyl groups, alkoxy groups, or perfluorinated hydrocarbyl groups are fluorine atoms.

8. A process as in claim 1 wherein the hydrocarbyl Grignard reagent is isopropylmagnesium bromide, wherein the polyhaloaromatic compound in a) is chloropentafluorobenzene, and wherein the polyhaloaromatic compound in b) is bromopentafluorobenzene.

9. A process as in claim 1 wherein (iii) in a) is at least predominately a liquid ethereal reaction medium.

10. A process as in claim 1 wherein (iii) in a) is diethyl ether.

11. A process as in claim 1 wherein in b) said amount of said at least one polyhaloaromatic compound is in excess relative to said excess hydrocarbyl Grignard reagent such that said reaction product mixture comprises an excess of said polyhaloaromatic compound.

12. A process as in claim 11 wherein said excess polyhaloaromatic compound in the reaction product mixture in b) is back-titrated with hydrocarbyl Grignard reagent.

13. A process as in claim 1 wherein the temperature of the mixture in a) and/or b) is in the range of from about 0° C. to about 60° C.

14. A process as in claim 1 wherein the pressure in a) and/or b) is in the range of from about 0 psig to about 20 psig.

15. A process as in claim 1 wherein the hydrocarbyl Grignard reagent is isopropylmagnesium bromide, wherein the polyhaloaromatic compound in a) is chloropentafluorobenzene, wherein the polyhaloaromatic compound in b) is bromopentafluorobenzene, wherein (iii) is a liquid ethereal reaction medium, and wherein the reaction product mixture produced in b) is composed predominately of pentafluorophenylmagnesium bromide, isopropyl chloride, isopropyl bromide, bromopentafluorobenzene and said liquid ethereal reaction medium.

16. A process as in claim 15 wherein said excess bromopentafluorobenzene in the reaction product mixture produced in b) is back-titrated with isopropylmagnesium bromide.

17. A process which comprises
   a) reacting, in a liquid organic reaction medium, at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, with a stoichiometric excess of a hydrocarbyl Grignard reagent to produce a reaction product mixture comprising perfluoroaryl Grignard reagent and unreacted hydrocarbyl Grignard reagent; and
   b) contacting at least a portion of the reaction product mixture produced in a) with a polyhaloaromatic compound to convert at least a portion of said unreacted hydrocarbyl Grignard reagent into perfluoroaryl Grignard reagent.

18. A process according to claim 17 wherein said liquid organic medium is ether.

19. A process according to claim 17 wherein said perhaloaromatic compound in a) is chloropentafluorobenzene.

20. A process according to claim 17 wherein said hydrocarbyl Grignard reagent is isopropyl magnesium bromide.

21. A process according to claim 17 wherein said perhaloaromatic compound in b) is bromopentafluorobenzene.

22. A process according to claim 17 wherein the reaction temperature is in the range of from about 0° C. to about 60° C.

23. A process according to claim 17 wherein the pressure is in the range of from about 0 psig to about 20 psig.

24. A process which comprises
   a) contacting a mixture comprising a perfluoroaryl Grignard reagent, a hydrocarbyl Grignard reagent, and a liquid organic medium, with at least one polyhaloaromatic compound in which one position on the aromatic ring(s) is substituted by a fluorine atom or a halogen atom other than a fluorine atom, and in which each of the other positions on the aromatic ring(s) is substituted by a fluorine atom, a hydrocarbyl group, an alkoxy group, or a perfluorinated hydrocarbyl group, in an amount at least equivalent to the amount of said hydrocarbyl Grignard reagent, and
   b) maintaining the resultant mixture at a temperature at least high enough to cause hydrocarbyl Grignard reagent to be converted into perfluoroaryl Grignard reagent.

25. A process according to claim 24 wherein said perfluoroaryl Grignard reagent is pentafluorophenylmagnesium bromide.

26. A process according to claim 24 wherein said hydrocarbyl Grignard reagent is isopropylmagnesium bromide.

27. A process according to claim 24 wherein at least the mixture of a) comprises at least one ether.

28. A process according to claim 24 wherein in a) the polyhaloaromatic compound is introduced into said mixture comprising perfluoroaryl Grignard reagent, hydrocarbyl Grignard reagent, and liquid organic medium.

29. A process according to claim 24 wherein the polyhaloaromatic compound is bromopentafluorobenzene.

30. A process according to claim 24 wherein the temperature in b) is in the range of from about 0° C. to about 60° C.

31. A process according to claim 24 wherein the pressure is in the range of from about 0 psig to about 20 psig.

32. A process which comprises:
   a) forming a mixture comprising (i) hydrocarbyl Grignard reagent, (ii) at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, and (iii) an anhydrous liquid organic reaction medium, in which the molar ratio of (i) to (ii) is greater than 1, such that a reaction product mixture is formed comprising perfluoroaryl Grignard reagent and excess hydrocarbyl Grignard reagent;
   b) mixing with at least a portion of said reaction product mixture produced in a) an amount of at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, said amount being in excess relative to said hydrocarbyl Grignard reagent such that there is produced a further reaction product mixture composed predominately of perfluoroaryl Grignard reagent, anhydrous liquid organic reaction medium, and unreacted polyhaloaromatic compound; and
   c) mixing a boron trihalide or a boron trihalide-solvent complex with at least a portion of said reaction product mixture produced in b) in proportions such that a tris(perfluoroaryl)borane is produced.

33. A process as in claim 32 wherein the boron trihalide is boron trifluoride or a boron trifluoride-solvent complex.

34. A process as in claim 32 wherein in c) said proportions are such that the molar ratio of perfluoroaryl Grignard reagent to boron trihalide is in the range of about 2.7:1 to about 3.3:1.

35. A process as in claim 32 wherein the solvent in which the boron trihalide or boron trihalide-solvent complex is dissolved is an ether-containing medium.

36. A process as in claim 32 in which the temperature during initial mixing of the boron trihalide and the reaction product mixture produced in b) containing the perfluoroaryl Grignard reagent is in the range of from about −20° C. to about 5° C.

37. A process as in claim 36 in which the temperature in c) after initial mixing is in the range of from about −15° C. to about 40° C.

38. A process as in claim 32 in which at least a portion of said unreacted polyhaloaromatic compound is recovered from c) and recycled to a) and/or b) after the tris (perfluoroaryl)borane is produced.

39. A process as in claim 32 in which other polyhaloaromatic compounds than said unreacted polyhaloaromatic compound present in c) are recovered after the tris (perfluoroaryl)borane is produced.

40. A process as in claim 32 wherein the hydrocarbyl Grignard reagent is isopropylmagnesium bromide, wherein the polyhaloaromatic compound in a) is chloropentafluorobenzene, wherein the polyhaloaromatic compound in b) is bromopentafluorobenzene, wherein (iii) is a liquid ethereal reaction medium, wherein the reaction product mixture produced in b) is composed predominately of pentafluorophenylmagnesium bromide, isopropyl chloride, isopropyl bromide, bromopentafluorobenzene and said liquid ethereal reaction medium, wherein the bromopentafluorobenzene in the reaction product mixture produced in b) is consumed by back-titration with isopropylmagnesium bromide prior to step c); and wherein said boron trihalide is boron trifluoride or a boron trifluoride etherate.

41. A process as in claim 40 wherein in c) said proportions are such that the molar ratio of pentafluorophenyl Grignard reagent to boron trifluoride is in the range of about 2.7:1 to about 3.3:1.

42. A process which comprises:
   a) forming a mixture comprising (i) hydrocarbyl Grignard reagent, (ii) at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, and (iii) an anhydrous liquid organic reaction medium, in which the molar ratio of (i) to (ii) is greater than 1, such that a reaction product mixture is formed comprising perfluoroaryl Grignard reagent and excess hydrocarbyl Grignard reagent;
   b) mixing with at least a portion of said reaction product mixture produced in a) an amount of at least one polyhaloaromatic compound in which one position on the aromatic ring(s) is substituted by a hydrogen atom or a halogen atom other than a fluorine atom, and in which each of the other positions on the aromatic ring(s) is substituted by a fluorine atom, a hydrocarbyl group, an alkoxy group, or a perfluorinated hydrocarbyl group, said amount being in excess relative to said hydrocarbyl Grignard reagent such that there is produced a further reaction product mixture composed predominately of perfluoroaryl Grignard reagent, anhydrous liquid organic reaction medium, and unreacted polyhaloaromatic compound; and
   c) mixing a boron trihalide or a boron trihalide-solvent complex with at least a portion of said reaction product mixture produced in b) in proportions such that a salt of a tetrakis(perfluoroaryl)borate anion is produced.

43. A process as in claim 42 wherein the boron trihalide is boron trifluoride or a boron trifluoride-solvent complex.

44. A process as in claim 42 wherein in c) said proportions are such that the molar ratio of perfluoroaryl Grignard reagent to boron trihalide is in the range of about 3.8:1 to about 7:1.

45. A process as in claim 42 wherein the solvent in which the boron trihalide or boron trihalide-solvent complex is dissolved is an ether-containing medium.

46. A process as in claim 42 in which the temperature during initial mixing of the boron trihalide and the reaction product mixture produced in b) containing the perfluoroaryl Grignard reagent is in the range of from about 0° C. to about 50° C.

47. A process as in claim 46 in which the temperature in step c) after initial mixing is in the range of from about 20° C. to about 60° C.

48. A process according to claim 42 wherein the pressure is in the range of from about 0 psig to about 20 psig.

49. A process as in claim 42 in which at least a portion of said unreacted polyhaloaromatic compound is recovered from c) and recycled to a) and/or b) after the tetrakis (perfluoroaryl)borate anion is produced.

50. A process as in claim 42 in which other polyhaloaromatic compounds than said unreacted polyhaloaromatic compound present in c) are recovered after the tetrakis (perfluoroaryl)borate anion is produced.

51. A process as in claim 42 wherein the hydrocarbyl Grignard reagent is isopropylmagnesium bromide, wherein the polyhaloaromatic compound in a) is chloropentafluorobenzene, wherein the polyhaloaromatic compound in b) is bromopentafluorobenzene, wherein (iii) is a liquid ethereal reaction medium, wherein the reaction product mixture produced in b) is composed predominately of pentafluorophenylmagnesium bromide, isopropyl chloride, isopropyl bromide, bromopentafluorobenzene and said liquid ethereal reaction medium, wherein the bromopentafluorobenzene in the reaction product mixture produced in b) is consumed by back-titration with isopropylmagnesium bromide prior to step c); and wherein said boron trihalide is boron trifluoride or a boron trifluoride-solvent complex.

52. A process as in claim 51 wherein in c) said proportions are such that the molar ratio of pentafluorophenyl Grignard reagent to boron trifluoride is in the range of about 3.8:1 to about 7:1.

* * * * *